US012736534B2

(12) United States Patent
Yamanaka et al.

(10) Patent No.: US 12,736,534 B2
(45) Date of Patent: Sep. 15, 2026

(54) METHOD FOR DETECTING AND QUANTIFYING BETA-1,6-BRANCHED BETA-1,3-GLUCAN OR BETA-1,3-GLUCAN, AND KIT FOR DETECTING AND QUANTIFYING THE SAME

(71) Applicant: TOEI SHINYAKU CO., LTD., Tokyo (JP)

(72) Inventors: Daisuke Yamanaka, Tokyo (JP); Yoshiyuki Adachi, Tokyo (JP)

(73) Assignee: TOEI SHINYAKU CO., LTD., Tokyo (JP)

( * ) Notice: Subject to any disclaimer, the term of this patent is extended or adjusted under 35 U.S.C. 154(b) by 951 days.

(21) Appl. No.: 17/910,526

(22) PCT Filed: Sep. 1, 2021

(86) PCT No.: PCT/JP2021/032154
§ 371 (c)(1),
(2) Date: Sep. 9, 2022

(87) PCT Pub. No.: WO2022/050316
PCT Pub. Date: Mar. 10, 2022

(65) Prior Publication Data

US 2023/0135638 A1 May 4, 2023

(30) Foreign Application Priority Data

Sep. 7, 2020 (JP) ................................ 2020-149797

(51) Int. Cl.
*G01N 33/569* (2006.01)

(52) U.S. Cl.
CPC ... *G01N 33/56961* (2013.01); *G01N 2400/24* (2013.01)

(58) Field of Classification Search
None
See application file for complete search history.

(56) References Cited

U.S. PATENT DOCUMENTS 4,208,479 A * 6/1980 Zuk ...................... C07J 41/0016 436/826
2021/0155970 A1 5/2021 Yamanaka et al.

OTHER PUBLICATIONS

Yamanaka et al., Split Enzyme-Based Biosensors for Structural Characterization of Soluble and Insoluble β-Glucans, International Journal of Molecular Sciences, 22, (Feb. 2021), (15 pages). (Year: 2021).*
International Search Report issued Nov. 16, 2021 in International (PCT) Application No. PCT/JP2021/032154.
Adachi, Y. et al., "Detection of immunomodulatory polysaccharides in food materials using the enzyme-fused innate immune receptors", European Journal of Immunology, 2016, vol. 46 (Suppl. 1), Abstract No. 1281.

* cited by examiner

*Primary Examiner* — Ellen J Marcsisin
(74) *Attorney, Agent, or Firm* — Wenderoth, Lind & Ponack, L.L.P.

(57) ABSTRACT

In a first step, when a β-1,6-branched β-1,3-glucan is contained in a test specimen, an active reporter protein comprising one and the other of split reporter proteins is formed by binding the β-1,6-branched β-1,3-glucan to a first fusion protein and a second fusion protein, and when a β-1,3-glucan is contained in the test specimen, the active reporter protein comprising one and the other of the split reporter proteins is formed by binding the β-1,3-glucan to the first fusion protein and a third fusion protein, and in a second step, the active reporter protein formed in the first step is detected and quantified.

5 Claims, 9 Drawing Sheets

Specification includes a Sequence Listing.

A

B

METHOD FOR DETECTING AND QUANTIFYING BETA-1,6-BRANCHED BETA-1,3-GLUCAN OR BETA-1,3-GLUCAN, AND KIT FOR DETECTING AND QUANTIFYING THE SAME

TECHNICAL FIELD

The present invention relates to a method for detecting and quantifying a β-1,6-branched β-1,3-glucan or a β-1,3-glucan and a kit for detecting and quantifying the same.

BACKGROUND ART

β-glucans are contained in a large amount in cell walls and cells of yeasts, algae, mushrooms, molds, lactic acid bacteria, bacteria, lichens, other microorganisms, and the like, and are sometimes secreted outside cell bodies as soluble molecules. β-glucans exhibit a strong immune-enhancing action, and have been applied to food, cosmetics, and feed. In particular, soluble β-glucans derived from basidiomycetes have been used as pharmaceuticals in Japan.

Among polysaccharides produced by basidiomycetes such as mushrooms and yeasts, it is known that a β-1,6-branched β-1,3-glucan having a β-1,3-glucoside bond in the main chain and a β-1,6-glucoside bond in the side chain exhibits particularly characteristic physiological activity.

In order to analyze and evaluate the structure of these β-glucans, analysis methods such as nuclear magnetic resonance (NMR), high performance liquid chromatography (HPLC), and gas chromatograph (GC) are suitable, but for this purpose, advanced purification methods including complicated steps are required. In addition, in such analysis methods, it is necessary to purify soluble β-glucans, which has been unsuitable for analysis of a partially purified specimen.

Thus, a plurality of methods for quantifying β-1,3-/β-1,6-glucans contained in a partially purified specimen have been developed. Many of them are a method combining a carbohydrate-degrading enzyme such as α-glucanase, β-1,3-glucanase, or β-1,6-glucanase and an acid-hydrolysis method such as a sulfuric acid method, and it is possible to estimate the amount of β-1,3-/β-1,6-glucans contained in a test specimen regardless of the insolubility or solubility of the subject by quantifying the amount of glucose produced (for example, Patent Literature 1).

In addition, a method for quantifying a β-1,3-glucan and a method for quantifying a β-1,6-glucan have also been developed.

A known method for quantifying a β-1,3-glucan includes a limulus method using a body fluid of a horseshoe crab, an enzyme method, or an ELISA-based quantification method in which a horseshoe crab-derived β-glucan-binding protein, an antibody, dectin-1, which is a mammalian β-glucan receptor, an insect β-glucan recognition protein (BGRP), glycosphingolipid, and the like are combined, or the like (for example, Patent Literatures 2, 3, and 4, and Non Patent Literatures 1, 2, 3, and 4).

A known method for quantifying a β-1,6-glucan includes an enzyme method, or an ELISA-based quantification method in which an antibody, a lectin, a β-1,6-glucanase mutant having specific binding activity to a β-1,6-glucan, and the like are combined, or the like (for example, Non Patent Literature 5).

Furthermore, by combining these β-1,3-glucan-binding proteins and β-1,6-glucan-binding proteins and constructing a sandwich ELISA-based quantification method, it is also possible to quantify a β-1,6-branched β-1,3-glucan.

CITATION LIST

Patent Literature

Patent Literature 1: JP 5467251 B2
Patent Literature 2: WO 92/16651 A
Patent Literature 3: U.S. Pat. No. 9,885,726 B2
Patent Literature 4: WO 2010/107068 A
Patent Literature 5: WO 2018/212095 A

Non Patent Literature

Non Patent Literature 1: Appl Environ Microbiol. 2001 December; 67 (12): 5420-5424.

Non Patent Literature 2: Int J Mol Sci. 2019 Jul. 16; 20(14): 3498.

Non Patent Literature 3: J Immunol Methods. 2006 Jul. 31; 314 (1-2): 164-9.

Non Patent Literature 4: J Immunol Methods. 2011 Feb. 28; 365 (1-2): 158-65.

Non Patent Literature 5: J Biol Chem. 2020 Apr. 17; 295 (16): 5362-5376.

SUMMARY OF INVENTION

Technical Problem

However, the method of Patent Literature 1 is a quantification method using an enzyme, and does not detect a branch of a β-glucan (a β-1,3-glucan having a side chain by a β-1,6-glucoside bond in one molecule). In addition, in the ELISA-based quantification method, a soluble β-glucan can be quantified, but an insoluble β-glucan cannot be quantified because a plurality of washing steps are required.

The present invention has been made in view of the above circumstances, and it is an object of the present invention to provide a method and a kit capable of efficiently detecting and quantifying a β-1,6-branched β-1,3-glucan or a β-1,3-glucan without requiring a washing step or the like regardless of the purification purity and the properties such as solubility and insolubility of a β-glucan.

Solution to Problem

In order to solve the above problems, a method for detecting and quantifying a β-1,6-branched β-1,3-glucan or a β-1,3-glucan of the present invention includes:

- a first step of bringing a test specimen into contact with a reagent; and
- a second step of detecting and quantifying a product in the first step,
- wherein the reagent contains:
- a first fusion protein having a split reporter protein; and
- any of a second fusion protein and a third fusion protein each having a split reporter protein,
- the split reporter protein is capable of forming an active reporter protein by making a pair of separated two of the split reporter proteins,
- the first fusion protein includes a β-1,3-glucan-binding protein and one of the split reporter proteins,
- the second fusion protein includes a β-1,6-glucan-binding protein and the other of the split reporter proteins,
- the third fusion protein includes a β-1,3-glucan-binding protein and the other of the split reporter proteins, in the first step, when a β-1,6-branched β-1,3-glucan is contained in the test specimen, the active reporter protein comprising one and the other of the split reporter proteins is formed by binding the β-1,6-branched β-1,3-glucan to the first fusion protein and the second fusion protein, when a β-1,3-glucan is contained in the test specimen, the active reporter protein comprising one and the other of the split reporter proteins is formed by binding the β-1,3-glucan to the first fusion protein and the third fusion protein, and in the second step, the active reporter protein formed in the first step is detected and quantified.

A kit for detecting and quantifying a β-1,6-branched β-1,3-glucan or a β-1,3-glucan of the present invention includes a reagent containing:

a first fusion protein having a split reporter protein; and any of a second fusion protein and a third fusion protein each having a split reporter protein, wherein the split reporter protein is capable of forming an active reporter protein by making a pair of separated two of the split reporter proteins, the first fusion protein includes a β-1,3-glucan-binding protein and one of the split reporter proteins, the second fusion protein includes a β-1,6-glucan-binding protein and the other of the split reporter proteins, the third fusion protein includes a β-1,3-glucan-binding protein and the other of the split reporter proteins, the active reporter protein comprising one and the other of the split reporter proteins can be formed by binding a β-1,6-branched β-1,3-glucan to the first fusion protein and the second fusion protein, and the active reporter protein comprising one and the other of the split reporter proteins can be formed by binding a β-1,3-glucan to the first fusion protein and the third fusion protein.

Advantageous Effects of Invention

According to the method for detecting and quantifying a β-1,6-branched β-1,3-glucan or a β-1,3-glucan and the kit for detecting and quantifying the same of the present invention, it is possible to efficiently detect and quantify a β-1,6-branched β-1,3-glucan or a β-1,3-glucan without requiring a washing step regardless of the purification purity and the properties such as solubility and insolubility of a β-glucan.

DESCRIPTION OF EMBODIMENTS

Figure 1:
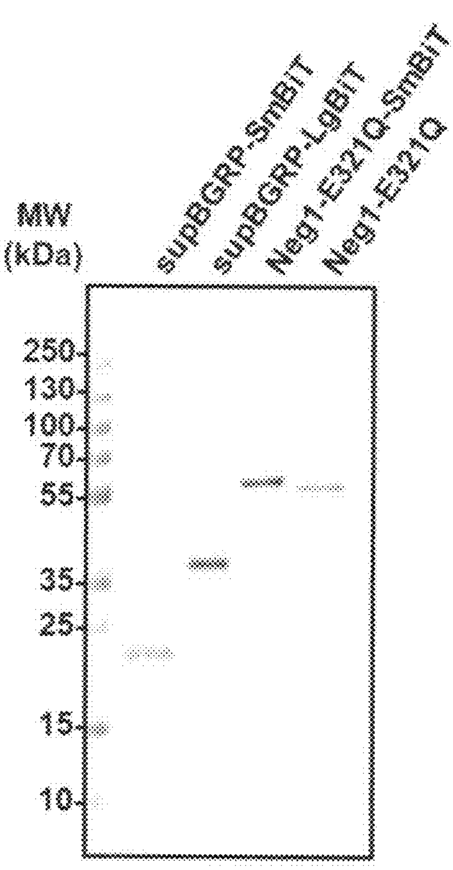
FIG. 1 shows the results of polyacrylamide electrophoresis of split reporter protein-fused supBGRP (first and third fusion proteins) and a split reporter protein-fused β-1,6-glucanase mutant (second fusion protein), followed by CBB staining.

Hereinafter, an embodiment of a method for detecting and quantifying a β-1,6-branched β-1,3-glucan or a β-1,3-glucan of the present invention will be described.

The method for detecting and quantifying a β-1,6-branched β-1,3-glucan or a β-1,3-glucan of the present invention (hereinafter, it may be simply referred to as "detection and quantification method" or "protein-fragment complementation assay") includes: a first step of bringing a test specimen into contact with a reagent; and a second step of detecting and quantifying a product in the first step.

(First Step)

In the first step, a test specimen and a reagent are brought into contact with each other.

The test specimen may contain a purified or partially purified β-1,6-branched β-1,3-glucan or β-1,3-glucan, and the property thereof may be either soluble or insoluble.

In addition, the substance contained in the test specimen is not particularly limited, and examples thereof include cell walls and extracts of basidiomycetes such as mushrooms, bacteria, yeasts, seaweeds, and plants, β-glucans secreted outside cell bodies, and β-glucans present in environments such as indoors, soils, rivers, seawater, the atmosphere, and space.

The reagent contains:

a first fusion protein having a split reporter protein; and any of a second fusion protein having a split reporter protein and a third fusion protein having a split reporter protein.

That is, the reagent contains a combination of the first fusion protein and the second fusion protein and/or a combination of the first fusion protein and the third fusion protein.

As used herein, the split reporter protein means a reporter protein divided into two, and the separated two are paired (in proximity or bound) to form an active reporter protein.

Specifically, in a state in which each of the split reporter proteins is present separately, it does not exhibit a function as a reporter protein. However, when one and the other of the split reporter proteins are in proximity or bound to each other, they exhibit a function as a reporter protein.

The structure of the split reporter protein is not specifically limited as long as it is identifiable when one and the other of the split reporter proteins are in proximity or bound to each other.

For example, the split reporter protein may be configured such that when one and the other of the split reporter proteins are in proximity to each other, structural complementarity is promoted to form an active reporter protein.

In addition, the split reporter protein may be configured such that when one and the other of the split reporter proteins are in proximity to each other, bioluminescence resonance energy transfer (BRET) or fluorescence resonance energy transfer (FRET) occurs. In this case, the active reporter protein refers to a reporter protein in which one and the other of the split reporter proteins are in proximity to each other to generate BRET or FRET. When the reporter protein generates BRET or FRET, the split reporter protein may be configured such that a fluorescent substance is bound to one or the other of the split reporter proteins.

Further, the split reporter protein may be configured such that when one and the other of the split reporter proteins are in proximity to each other, an active reporter protein is formed by protein splicing. This can be achieved by fusing protein-splicing domains to one and the other of the split reporter proteins. Examples of the protein-splicing domain include a combination of DnaEn and DnaEc, which are protein-splicing domains derived from a DnaE gene of *Synechocystis* sp.

More specific reporter proteins include enzymes, fluorescent proteins, and the like. Examples of the enzyme include luciferase, alkaline phosphatase, horseradish peroxidase, invertase, β-galactosidase, β-glucuronidase, and variants of these enzymes. Examples of the fluorescent protein include green fluorescent protein (GFP) and variants of GFP.

The first fusion protein includes a β-1,3-glucan-binding protein and one of the split reporter proteins.

The second fusion protein includes a β-1,6-glucan-binding protein and the other of the split reporter proteins.

The third fusion protein includes a β-1,3-glucan-binding protein and the other of the split reporter proteins.

The β-1,3-glucan-binding protein may be a known protein, and examples thereof include an antibody, dectin-1, a lectin, horseshoe crab factor G protein, insect β-glucan recognition protein (BGRP), supBGRP (described in Examples mentioned below), and derivatives thereof, and it is preferable that soluble recombinant protein expression is easy.

The β-1,6-glucan-binding protein may be a known protein, and examples thereof include an antibody, a lectin, a β-1,6-glucanase mutant having no cleavage activity of a β-1,6-glucan and having specific binding activity to a β-1,6-glucan, and derivatives thereof, and it is preferable that soluble recombinant protein expression is easy.

The detection and quantification method of the present invention can be performed by directly supplying a reagent containing the first fusion protein and the second fusion protein or a reagent containing the first fusion protein and the third fusion protein into a test tube containing a test specimen, or can be performed using a cell expressing these fusion proteins or the like. In this case, the expression of the first fusion protein and the second fusion protein or the expression of the first fusion protein and the third fusion protein may be transient expression or homeostatic expression. That is, cell lines stably expressing the first to third fusion proteins can be used.

Specifically, examples of the first to third fusion proteins can include those produced in *E. coli*, yeasts, plants, animal cells, and cell-free expression systems, and those produced in large amounts in *E. coli* are particularly easy to use and preferred. A partially purified solution such as a liquid of disrupted cells expressing the first to third fusion proteins may be used, but it is preferable to use a fusion protein obtained by fusing a general low molecular weight peptide tag and purifying the fusion protein with high purity by column purification or the like. In this case, a GST tag, a protein A tag, an antibody Fc region, a polyhistidine tag, a V5 tag, a Myc tag, an SBP tag, a Halo tag, a Strep tag, and the like can be exemplified. In addition, as the cell, an animal cell, an insect cell, a plant cell, and the like can be exemplified, and an established cell line is easy to use and preferred.

In the first fusion protein, one of the split reporter proteins may be fused to the N-terminal side of the β-1,3-glucan-binding protein, and one of the split reporter proteins may be fused to the C-terminal side of the β-1,3-glucan-binding protein. In the second fusion protein, the other of the split reporter proteins may be fused to the N-terminal side of the β-1,6-glucan-binding protein, and the other of the split reporter proteins may be fused to the C-terminal side of the β-1,6-glucan-binding protein. Furthermore, in the third fusion protein, the other of the split reporter proteins may be fused to the N-terminal side of the β-1,3-glucan-binding protein, and the other of the split reporter proteins may be fused to the C-terminal side of the β-1,3-glucan-binding protein. In this case, in the first fusion protein, the second fusion protein, and the third fusion protein, it is preferable to insert a linker peptide having an appropriately adjusted length in order to avoid steric hindrance when fusing the β-1,3-glucan-binding protein or the β-1,6-glucan-binding protein with the split reporter protein.

Here, examples of the linker peptide include a peptide having about 1 to 20 residues, and as the amino acid sequence thereof, an amino acid sequence that is the same as the amino acid sequence of a general linker used in production of a fusion protein can be exemplified. Specific examples thereof include a GS linker including a repeating sequence containing Gly-Ser, a DDAKK linker including a repeating sequence of Asp-Asp-Ala-Lys-Lys (SEQ ID NO: 1), and an EAAAK linker including a repeating sequence of Glu-Ala-Ala-Ala-Lys (SEQ ID NO: 2). In the first fusion protein, the second fusion protein, and the third fusion protein, the region to which one or the other of the split reporter proteins is fused is not limited to either the N-terminal side or the C-terminal side, and it is preferable to determine the region to be fused according to the characteristics of various β-1,3-glucan-binding proteins and β-1,6-glucan-binding proteins. Alternatively, the fusion protein may be a fusion protein in which the split reporter proteins are fused to both the N-terminal side and the C-terminal side.

Then, in the first step, when a β-1,6-branched β-1,3-glucan is contained in the test specimen, the β-1,6-branched β-1,3-glucan is bound to the first fusion protein and the second fusion protein, whereby one and the other of the split reporter proteins are in proximity or bound to each other to form an active reporter protein.

In addition, when a β-1,3-glucan (including a β-1,3-glucan having a side chain (branch)) is contained in the test specimen, the β-1,3-glucan is bound to the first fusion protein and the third fusion protein, whereby one and the other of the split reporter proteins are in proximity or bound to each other to form an active reporter protein.

(Second Step)

In the second step, the active reporter protein formed in the first step is detected and quantified. Higher activity of the reporter protein than that in the absence of a β-1,6-branched β-1,3-glucan or a β-1,3-glucan indicates that a β-1,6-branched β-1,3-glucan or a β-1,3-glucan is present in the test specimen. As a result, a β-1,6-branched β-1,3-glucan or a β-1,3-glucan contained in the test specimen can be easily detected and quantified. The detection and quantification method is not particularly limited, and a known method can be appropriately adopted depending on the form of the reporter protein and the like.

As mentioned below in Examples, the difference between the activity (background) of a nonactivated reporter protein observed in the absence of a β-glucan having a structure of interest and the activity of a reporter protein reconstituted in the presence of a β-glucan is about 100 times, showing high sensitivity.

In addition, in the detection and quantification method of the present invention, complicated washing operations and the like are unnecessary, and β-glucans contained in the test specimen can be screened for structures of the 1-glucans at high throughput. Therefore, by applying the detection and quantification method of the present invention, various β-glucans derived from various species and extraction and purification methods and exhibiting various forms including soluble and insoluble (e.g., gel-like and particulate) forms can be widely analyzed under the same conditions, and screened for a more beneficial β-1,6-branched β-1,3-glucan or β-1,3-glucan. In addition, the detection and quantification method of the present invention does not require a step of washing a test specimen or the like, and can efficiently detect and quantify a β-1,6-branched β-1,3-glucan or a β-1,3-glucan.

Furthermore, for example, for the same test specimen, by comparing the activity of the active reporter protein by binding of a β-1,6-branched β-1,3-glucan to the first fusion protein and the second fusion protein with the activity of the active reporter protein by binding of a β-1,3-glucan to the first fusion protein and the third fusion protein, a β-1,3-glucan not having a β-1,6-branch can also be quantified.

Next, an embodiment of a kit for detecting and quantifying a β-1,6-branched β-1,3-glucan or a β-1,3-glucan of the present invention will be described. In the detection and quantification kit of the present invention, description of contents common to the above-mentioned detection and quantification method is partially omitted.

The detection and quantification kit of the present invention is a kit for detecting and quantifying a β-1,6-branched β-1,3-glucan or a β-1,3-glucan, the kit including a reagent containing:

a first fusion protein having a split reporter protein; and any of a second fusion protein and a third fusion protein each having a split reporter protein.

The split reporter protein is capable of forming an active reporter protein by making a pair of two of the split reporter proteins (in proximity or bound).

The first fusion protein includes a β-1,3-glucan-binding protein and one of the split reporter proteins.

The second fusion protein includes a β-1,6-glucan-binding protein and the other of the split reporter proteins.

The third fusion protein includes a β-1,3-glucan-binding protein and the other of the split reporter proteins.

By binding a β-1,6-branched β-1,3-glucan to the first fusion protein and the second fusion protein, it is possible to form an active reporter protein comprising one and the other of the split reporter proteins.

By binding a β-1,3-glucan to the first fusion protein and the third fusion protein, it is possible to form an active reporter protein comprising one and the other of the split reporter proteins.

The detection and quantification kit of the present invention can include, in addition to the above reagent, various materials and devices for detecting and quantifying a β-1,6-branched β-1,3-glucan or a β-1,3-glucan, and the like.

The method for detecting and quantifying a β-1,6-branched β-1,3-glucan or a β-1,3-glucan and the kit for detecting and quantifying the same of the present invention are not limited to the above embodiments.

EXAMPLES

Hereinafter, the present invention will be described with reference to Examples, but the method for detecting and quantifying a β-1,6-branched β-1,3-glucan or a β-1,3-glucan and the kit for detecting and quantifying the same of the present invention are not limited to the following Examples.

<Example 1> Production of Fusion Protein

An expression vector for a first fusion protein, an expression vector for a second fusion protein, and an expression vector for a third fusion protein were produced on the basis of a pColdl vector (manufactured by Takara Bio Inc.). These were transformed into *E. coli* Shuffle (manufactured by New England Biolabs) or BL 21 (DE3), and then expressed in large amounts in an ampicillin-added LB medium as a 6-histidine tag (His-Tag) fusion protein. After purification using TALON Metal Affinity Resin (manufactured by Takara Bio Inc.), the presence of the purified protein was confirmed by SDS-PAGE (FIG. 1).

As a β-1,3-glucan-binding protein, supBGRP produced based on insect-derived BGRP was used. The amino acid sequence of supBGRP is a β-1,3-glucan-binding protein artificially produced by introducing an amino acid mutation of about 36 residues (23 residues for silkworms) based on an amino acid sequence of a conventionally known β-glucan-binding protein (BGRP) derived from various insects such as silkworms and previous findings by the present inventors.

The amino acid sequence and the DNA sequence of supBGRP are shown below.

```
                                        (SEQ ID NO: 3)
Met Asn His Lys Val His His His His His

His Ile Glu Gly Arg His Met Glu Leu Gly

Thr Tyr Glu Val Pro Asp Ala Lys Leu Glu

Ala Ile Tyr Pro Lys Gly Leu Arg Val Ser

Ile Pro Asp Asp Gly Phe Ser Leu Phe Ala

Phe His Gly Lys Leu Asn Glu Glu Met Glu

Gly Leu Glu Ala Gly Thr Trp Ser Arg Asp

Ile Thr Lys Ala Lys Asn Gly Arg Trp Thr

Phe Arg Asp Arg Asn Ala Glu Leu Lys Ile

Gly Asp Lys Ile Tyr Phe Trp Thr Tyr Val
```

-continued

```
Ile Lys Asp Gly Leu Gly Tyr Arg Gln Asp

Asn Gly Glu Trp Thr Val Thr Gly Tyr Val

Asp Glu Asp Gly Asn Pro Val Asp Thr Asp

Gly Pro Thr Thr Thr Pro Thr Gly Ser Glu

Phe Lys Leu Val Asp Leu Gln Ser Arg

                                   (SEQ ID NO: 4)
atg aat cac aaa gtg cat cat cat cat cat

cat atc gaa ggt agg cat atg gag ctc ggt

acc tat gaa gtg cct gat gcg aaa ctc gaa

gcc att tac ccc aaa ggg tta cgc gtt agc

att ccg gat gat ggc ttt tcg ctg ttt gcc

ttc cat ggg aaa ctg aac gag gag atg gaa

ggt ctg gaa gct gga act tgg agt cgg gac

atc acg aaa gcg aag aac ggt cat tgg acc

ttt cgt gac cgc aat gca gag ctg aaa att

ggc gac aag atc tac ttc tgg acc tac gtc

atc aaa gat ggc ttg ggt tat cgc cag gat

aac gga gaa tgg acc gta acg ggc tat gtg

gac gaa gat ggc aat ccg gtt gat acc gat

ggt ccg act acg aca cca acc gga tcc gaa

ttc aag ctt gtc gac ctg cag tct aga tag
```

As a β-1,6-glucan-binding protein, a mutant of β-1,6-glucanase derived from *Neurospora crassa* (Neg1-E321Q) was used (Patent Literature 5).

As a reporter protein, luciferase derived from a deep-sea shrimp (*Oplophorus gracilirostris*) (NanoLuc, manufactured by Promega Corporation) was used. The split reporter protein used here (NanoLuc) is composed of two subunits, a large fragment called LgBiT and a small fragment called SmBiT, and these two subunits form a complex to reconstitute activated luciferase. Thus, the combination of LgBiT and SmBiT constitutes a combination of one and the other of the split reporter proteins.

In this example, as the first fusion protein, a fusion protein in which LgBiT was fused to the N-terminal side of supBGRP with a (DDAKK)4 sequence as a linker peptide being sandwiched therebetween (supBGRP-LgBiT) was produced. In addition, as the second fusion protein, a fusion protein in which SmBiT was fused to the N-terminal side of Neg1-E321Q with a GGSGGGSGG sequence (SEQ ID NO: 5) as a linker peptide being sandwiched therebetween (Neg1-E321Q-SmBiT) was produced. Furthermore, as the third fusion protein, a fusion protein in which SmBiT was fused to the N-terminal side of supBGRP with a (DDAKK)4 sequence as a linker peptide being sandwiched therebetween (supBGRP-SmBiT) was produced.

In order to confirm that the fusion proteins function and the activated reporter protein is reconstituted in the presence of a β-glucan, zymosan A, which is a partially purified particulate β-glucan derived from bakers yeasts, supBGRP-LgBiT, and Neg1-E321Q-SmBiT were mixed, and a NanoLuc substrate (NanoGlo, manufactured by Promega Corporation) was added to observe the presence or absence of bioluminescence.

Figure 2:
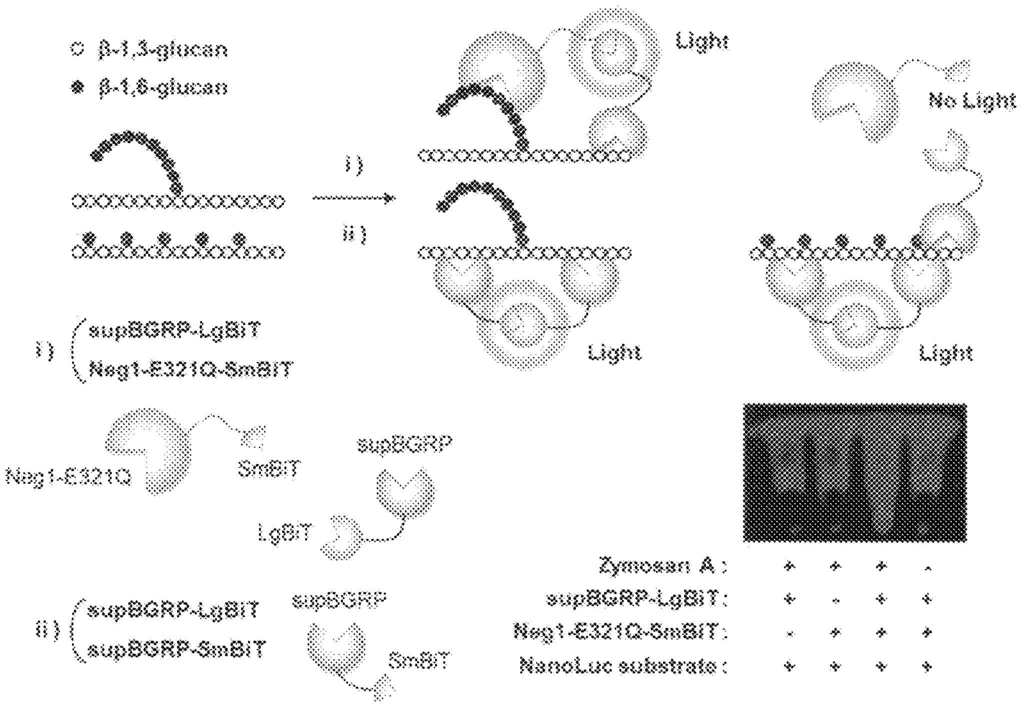
FIG. 2 shows the results of mixing split reporter protein-fused supBGRP (first and third fusion proteins) and a split reporter protein-fused β-1,6-glucanase mutant (second fusion protein) with a particulate β-glucan and an enzyme substrate, and observing the bioluminescence emitted by the activated split reporter protein (enzyme).

The results are shown in FIG. 2.

Bioluminescence was observed only when supBGRP-LgBiT, Neg1-E321Q-SmBiT, zymosan A. and the NanoLuc substrate were all present.

From these results, it was shown that the protein-fragment complementation assay can be used for simple structural analysis of β-glucans.

<Example 2> Study on Optimization of Protein-Fragment Complementation Assay

In order to construct and optimize a protein-fragment complementation assay that does not require a washing step, reactivity was examined by changing the concentration of glucan probes and the reaction time.

Figure 3:
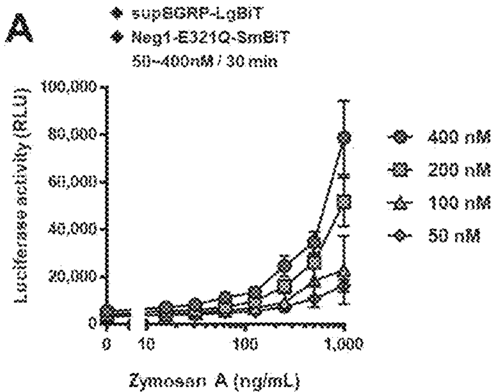
FIG. 3 shows the results of studying the influence of different concentrations and incubation times on the activation level of a split reporter protein (enzyme).
Figure 3:
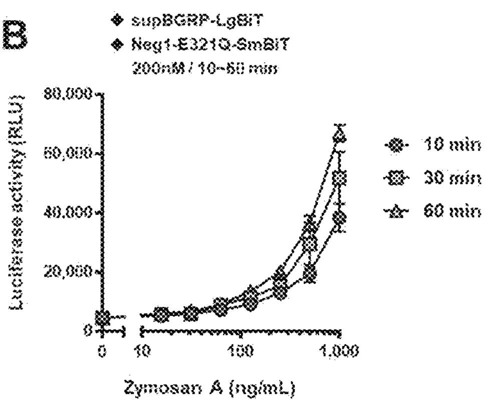

Mixed solutions (5 μL) with different concentrations (50, 100, 200, and 400 nM) of supBGRP-LgBiT and Neg1-E321Q-SmBiT were incubated with 10 μL of zymosan A (0 to 1,000 ng/mL) for 30 minutes in 96-well plates, and 15 μL of a NanoLuc substrate was added to evaluate the luciferase activity. As a result, as shown in FIG. 3A, it was confirmed that the luciferase activity increased in proportion to the concentration of each probe. Appropriate reaction curves were obtained in the presence of at least 200 nM of each probe.

Next, a 200-nM mixed solution of supBGRP-LgBiT and Neg1-E321Q-SmBiT (5 μL) was placed in a 96-well plate and incubated with 0 to 1,000 ng/mL of zymosan A (10 μL) for 10 minutes, 30 minutes, and 60 minutes, and 15 μL of a NanoLuc substrate was added to measure the luciferase activity. As a result, it was confirmed that incubation for 10 minutes was sufficient to obtain a reaction curve, but the luciferase activity increased when the incubation time was further increased (FIG. 3B).

<Example 3> Measurement of Various s-Glucans Using Fusion Protein

Five microliters of a mixed solution of the first fusion protein (supBGRP-LgBiT) and the second fusion protein (Neg1-E321Q-SmBiT) (200 nM each) or a mixed solution of the first fusion protein (supBGRP-LgBiT) and the third fusion protein (supBGRP-SmBiT) (200 nM each) and 10 μL of various polysaccharide specimens (0 to 50 μg/mL) were mixed in a 96-well plate (white flat bottom) and shaken on a plate shaker.

The polysaccharide specimens used are shown in Table 1.

TABLE 1

| Specimen | Structure | Origin |
|---|---|---|
| Zymosan A | β-1,6-/β-1,3-glucan | *Saccharomyces cerevisiae* |
| Curdlan | Linear β-1,3-glucan | *Alcaligenes faecalis* |
| Pustulan | β-1,6-glucan (with slight β-1,3-glucan) | *Lasallia pustulata* |
| Scleroglucan | β-1,6-/β-1,3-glucan | *Sclerotium rolfsii* |
| Paramylon | Linear β-1,3-glucan | *Euglena gracilis* |
| Pachyman | β-1,6-/β-1,3-glucan | *Wolfiporia extensa* |
| Laminarin | mono-β-1,6-/β-1,3-glucan | *Laminaria digitata* |
| HKCA | β-1,3-/β-1,6-glucan, others | *Candida albicans* |
| Chitin | β-1,4-poly-N-acetyl-d-glucosamine | Crab shell |
| Dextran | α-1,4-/α-1,6-glucan | *Leuconostoc mesenteroides* |
| Xylan | β-1,4-xylan backbone, others | Corn core |
| Mannan | α-1,6-/α-1,2-, α-1,3-mannan | *Saccharomyces cerevisiae* |

TABLE 1-continued

| Specimen | Structure | Origin |
|---|---|---|
| Depleted Zymosan | β-1,6-/β-1,3-glucan (insoluble) | *Saccharomyces cerevisiae* |
| CSBG | β-1,6-/β-1,3-glucan (soluble) | *Candida albicans* |

After 30 minutes, 15 μL of a NanoLuc substrate was added, and the bioluminescence level was measured with a luminometer (manufactured by Promega Corporation).

Figure 4:
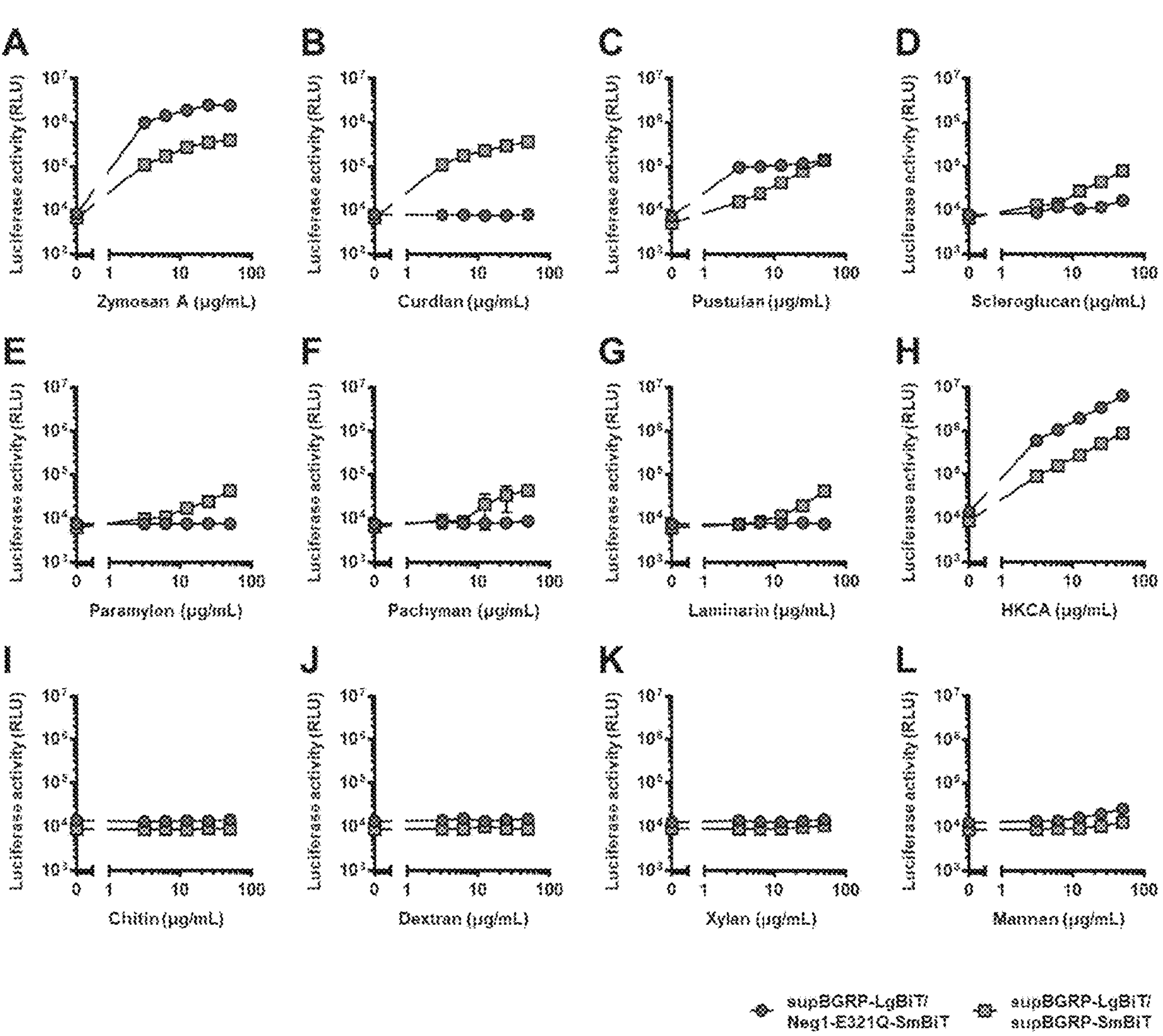
FIG. 4 shows the results of mixing various β-glucans, split reporter protein-fused supBGRP (first and third fusion proteins), and a split reporter protein-fused β-1,6-glucanase mutant (second fusion protein) with an enzyme substrate, and quantifying the bioluminescence emitted by the activated split reporter protein (enzyme).

The results are shown in FIG. 4.

In the combination of the first fusion protein (supBGRP-LgBiT) and the second fusion protein (Neg1-E321Q-SmBiT) (supBGRP-LgBiT/Neg1-E321Q-SmBiT), luminescence was observed in specimens containing a β-1,6-branched β-1,3-glucan, and in the combination of the first fusion protein (supBGRP-LgBiT) and the third fusion protein (supBGRP-SmBiT) (supBGRP-LgBiT/supBGRP-SmBiT), luminescence was observed in specimens containing a β-1,3-glucan.

Specific examples of the specimen containing a β-1,6-branched β-1,3-glucan include zymosan A, pustulan, scleroglucan, and heat-killed *C. albicans* (HKCA), and the mixed solution of the first fusion protein and the second fusion protein (supBGRP-LgBiT/Neg1-E321Q-SmBiT) showed reactivity with these specimens. It was shown that not only purified high-purity β-glucans but also HKCA, which is an unpurified specimen, can be detected by the same operation.

Meanwhile, specific examples of the specimen containing a β-1,3-glucan include zymosan A, curdlan, pustulan, scleroglucan, paramylon, pachyman, laminarin, and HKCA, and the mixed solution of the first fusion protein and the third fusion protein (supBGRP-LgBiT/supBGRP-SmBiT) showed reactivity with these specimens.

On the other hand, none of the mixed solutions showed reactivity with chitin, dextran, xylan, and mannan having no β-glucan structure.

From these results, it was confirmed that according to the method of the present invention, structural analysis of β-glucans in multiple specimens can be efficiently performed.

<Example 3> Structural Analysis of Natural Cell Walls of Fungi

In Example 2, it was demonstrated that the presence of β-1,3-glucans or long-chain β-1,6-branched-β-1,3-glucans on the surface of HKCA could be determined (FIG. 4H). However, HKCA does not necessarily mimic the natural cell wall composition of *C. albicans* because heat treatment often removes the mannan layer covering the surface of a β-glucan. Thus, it was examined whether the protein-fragment complementation assay can be applied to analysis of the natural cell wall structure of living fungi.

Figure 5:
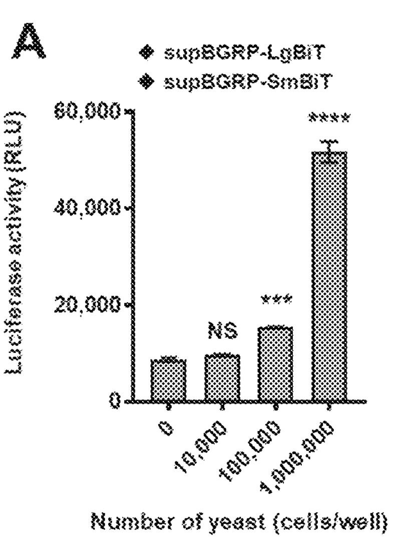
FIG. 5 shows the results of mixing live yeast-form *Candida albicans* with different cell numbers, split reporter protein-fused supBGRP (first and third fusion proteins), and a split reporter protein-fused β-1,6-glucanase mutant (second fusion protein) with an enzyme substrate, and quantifying the bioluminescence emitted by the activated split reporter protein (enzyme).
Figure 5:
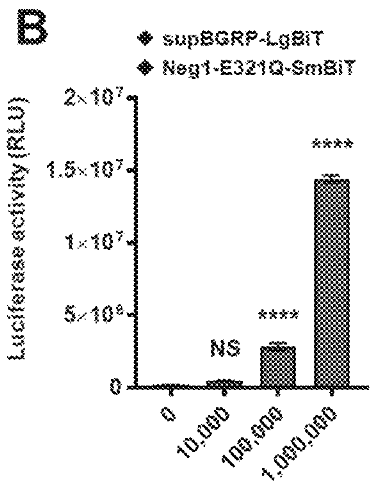

First, different numbers of yeast-form *C. albicans* (0, 104, 105, and 106 cells/well) were washed in a 96-well V-bottom plate and suspended in 10 μL of PBS. This was mixed with 5 μL of a mixed solution of the first fusion protein and the third fusion protein (supBGRP-LgBiT/supBGRP-SmBiT) or a mixed solution of the first fusion protein and the second fusion protein (supBGRP-LgBiT/Neg1-E321Q-SmBiT). After 30 minutes, 15 μL of a NanoLuc substrate was added, and the activation level of the reporter protein reconstituted on the living cell surface was measured, and as a result, in both supBGRP-LgBiT/supBGRP-SmBiT and supBGRP-LgBiT/Neg1-E321Q-SmBiT combinations, bioluminescence was significantly increased corresponding to 105 cells/well or more of yeast-form *C. albicans* (FIGS. 5A and 5B).

Figure 6:
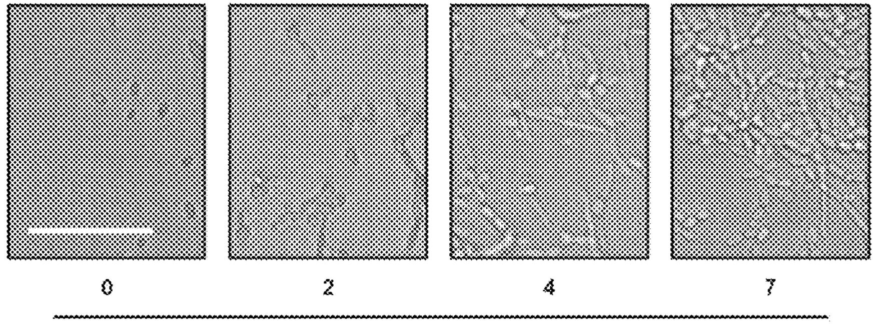
FIG. 6 is images showing the microscopic morphology of cultured *C. albicans*. The scale bar indicates 50 μm.

Next, using this method, the possibility of directly analyzing the cell wall glucan structure of hyphae-form *C. albicans*, which is generally difficult to analyze, was examined. To induce hyphae formation, yeast-form *C. albicans* (105 cells/well) was added to an RPMI 1640 medium containing 10% inactivated fetal bovine serum in a 96-well V-bottom plate and cultured at 37° C. for different times (0, 2, 4, and 7 hours). Hyphae formation was confirmed by parallel culturing *C. albicans* under the same conditions using a transparent 96-well flat bottom plate. The microscopic morphology of *C. albicans* at each culture time is shown in FIG. 6.

Figure 7:
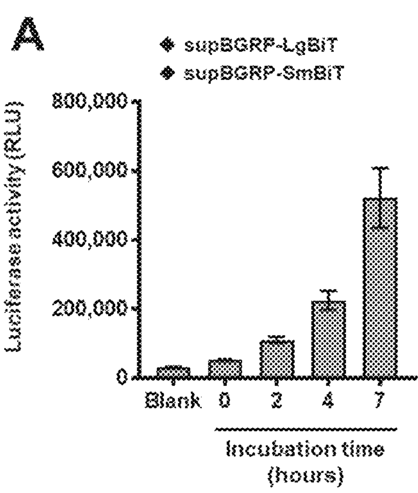
FIG. 7 shows the results of mixing *C. albicans* cultured for different times, split reporter protein-fused supBGRP (first and third fusion proteins), and a split reporter protein-fused β-1,6-glucanase mutant (second fusion protein) with an enzyme substrate, and quantifying the bioluminescence emitted by the activated split reporter protein (enzyme).
Figure 7:
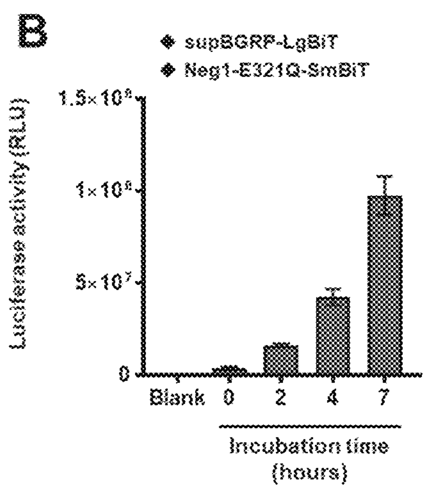

The washed hyphae were suspended in 10 μL of PBS and mixed with 5 μL of a mixed solution of the first fusion protein and the third fusion protein (supBGRP-LgBiT/supBGRP-SmBiT) or a mixed solution of the first fusion protein and the second fusion protein (supBGRP-LgBiT/Neg1-E321Q-SmBiT). After 30 minutes, a NanoLuc substrate (15 μL) was added and the bioluminescence level was measured. The luciferase activity, which indicates the amount of β-1,3-glucans or long-chain β-1,6-branched-β-1,3-glucans on the surface, significantly increased in a hyphae growth-dependent manner (FIGS. 7A and B). These results indicate that the present measurement method is useful for the analysis of glucan structure of untreated live fungal cell walls.

<Example 4> Application of Protein-Fragment Complementation Assay to Real-Time Monitoring of Structural Change of s-Glucan For example, the structure of a cell wall glucan is dynamically changed by the action of various enzymes during the growth process of the fungus. Thus, zymosan A, which is a particulate β-glucan, was treated with endo-β-1,6-glucanase (Neg1) or endo-β-1,3-glucanase (zymolyase) to examine whether the time-dependent change in the structure of a β-1,6-linked β-glucan side chain or a β-1,3-glucan chain could be evaluated by the present measurement method.

To 10 μL of zymosan A (10 μg/mL), 5 μL of a mixed solution of the first fusion protein and the third fusion protein (supBGRP-LgBiT/supBGRP-SmBiT) or a mixed solution of the first fusion protein and the second fusion protein (supBGRP-LgBiT/Neg1-E321Q-SmBiT) was added, and the solution was incubated for 60 minutes. A NanoLuc substrate (15 μL) containing PBS, endo-β-1,6-glucanase (final concentration of 0.5 μg/mL), or endo-β-1,3-glucanase (final concentration of 0.5 μg/mL) was added, and the reconstituted NanoLuc activity was measured 15 times every 2 minutes (for 30 minutes).

Figure 8:
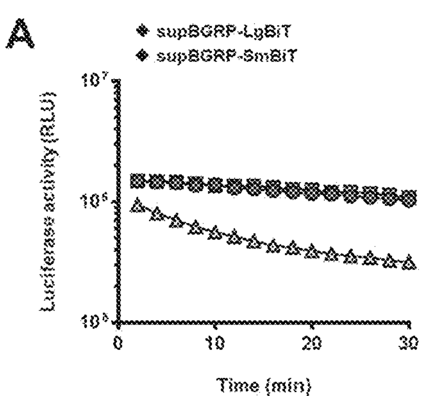
FIG. 8 shows the results of real-time monitoring of a change in side chain structure occurring during treatment of zymosan A, which is a particulate β-glucan, with various s-glucan-degrading enzymes, using a protein-fragment complementation assay.
Figure 8:
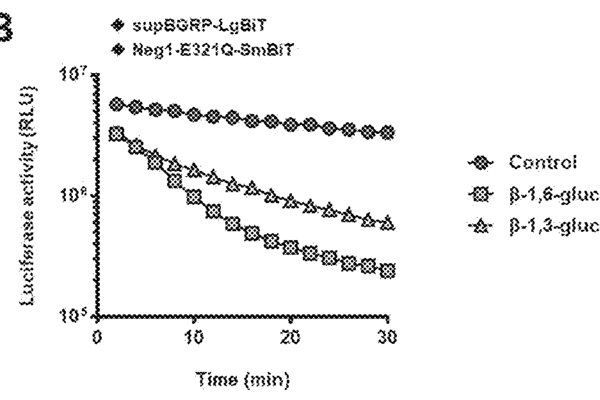

As shown in FIG. 8A, in the combination of the first fusion protein and the third fusion protein (supBGRP-LgBiT/supBGRP-SmBiT), in the untreated control sample, the luminescence intensity gradually decreased overtime (natural attenuation). Meanwhile, in the zymosan A treated with endo-β-1,3-glucanase, the luminescence intensity rapidly decreased, and the bioluminescence level (RLU measurement value) after 30 minutes was about ⅓ of that in the untreated group. Degradation of the β-1,6-linked side chain of zymosan A did not affect the glucan-binding capacity of supBGRP.

On the other hand, the activity of NanoLuc reconstituted from the combination of the first fusion protein and the second fusion protein (supBGRP-LgBiT/Neg1-E321Q-Sm- BiT) was dramatically decreased by treatment with endo-β-1,6-glucanase or endo-β-1,3-glucanase (FIG. 8B). The bioluminescence level (RLU measurement value) after 30 minutes was decreased to about $\frac{1}{6}$ in the endo-β-1,3-glucanase-treated group and about $\frac{1}{14}$ in the endo-β-1,6-glucanase-treated group compared with the untreated group. From these results, it was confirmed that the protein-fragment complementation assay was not only suitable for structural analysis of β-glucans, but also capable of monitoring a structural change of long-chain β-1,6-branched-β-1,3-glucans in real time.

<Example 5> Comparison of Reactivity Between Measurement Method Using Fusion Protein and Conventional ELISA Soluble and insoluble β-glucans were measured by a conventional ELISA method and a measurement method using a fusion protein, and the reactivity was compared between the methods. As the soluble β-glucan, an aqueous solution of CSBG purified from the *Candida* cell wall was used, and as the insoluble β-glucan, a suspension of depleted-zymosan (D-zymosan, InvivoGen) obtained by washing zymosan with a hot alkaline solution was used (Table 1).

Five microliters of a mixed solution of the first fusion protein (supBGRP-LgBiT) and the second fusion protein (Neg1-E321Q-SmBiT) (200 nM each) and 10 μL each of soluble and insoluble specimens (0 to 1,000 ng/mL) were mixed in a 96-well plate (white flat bottom) and shaken on a plate shaker. After 30 minutes, 15 μL of a NanoLuc substrate was added, and the bioluminescence level was measured with a luminometer (manufactured by Promega Corporation).

Figure 9:
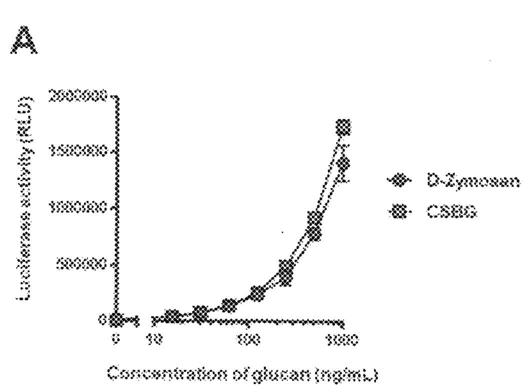
FIG. 9 shows the results of comparing the reactivity between a measurement method using split reporter proteins and a conventional ELISA method, each using CSBG, which is a soluble β-glucan, and D-zymosan, which is an insoluble β-glucan.
Figure 9:
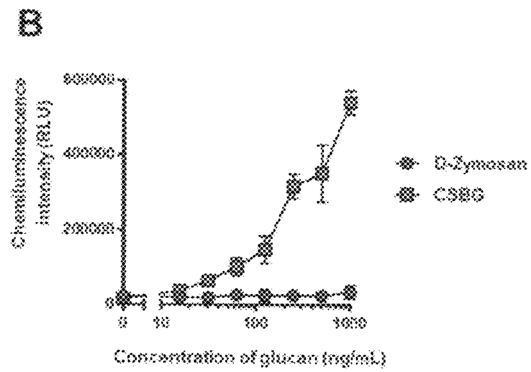

As shown in FIG. 9A, the enhancement of the reactivity depending on the addition concentration of a 0-glucan was confirmed regardless of whether the β-glucan was soluble or insoluble.

Meanwhile, the first fusion protein (supBGRP-LgBiT) was immobilized (2 μg/mL) on a 96-well plate (white flat bottom) and blocked with a PBS solution containing bovine serum albumin. After washing the plate, soluble and insoluble specimens (0 to 1,000 ng/mL) were added. After 60 minutes, washing was performed, and a biotin-labeled β-1,6-glucan-binding protein (Neg1-E321Q-Biotin, 2 μg/mL) was further added, and the resulting mixture was allowed to stand for 60 minutes. After washing, streptavidin-labeled horseradish peroxidase was added, and the mixture was allowed to stand for 20 minutes. After the plate was thoroughly washed, a commercially available luminescent substrate for peroxidase was added, and the luminescence level was measured with a luminometer (manufactured by Promega Corporation).

As shown in FIG. 9B, in the conventional ELISA method, an increase in the reactivity depending on the addition concentration was observed in CSBG, which is a soluble β-glucan, but reactivity was not shown in D-zymosan, which is an insoluble β-glucan.

From these results, it was confirmed that according to the method of the present invention, the amounts of soluble and insoluble β-glucans can be accurately measured under the same conditions.

The invention claimed is:

1. A method for detecting and quantifying a β-1,6-branched β-1,3-glucan or a β-1,3-glucan, the method comprising:

a first step of bringing a test specimen into contact with a reagent, wherein the reagent contains a reagent (A) and a reagent (B), wherein the reagent (A) comprises a first fusion protein, a second fusion protein and a split reporter protein that has a first subunit and other subunit, wherein the first and other subunits form a pair, and the first fusion protein is linked to the first subunit of the split reporter protein and the second fusion protein is linked to the other subunit of the split reporter protein, wherein the reagent (B) comprises the first fusion protein, a third fusion protein and the split reporter protein that has a first subunit and other subunit, the first fusion protein is linked to the first subunit of the split reporter protein, the third fusion protein is linked to the other subunit of the split reporter protein, wherein the first and other subunits of the split reporter protein form an active reporter protein by making a pair of the first and other subunits of the split reporter protein, the first fusion protein comprises a β-1,3-glucan-binding protein, the second fusion protein comprises a β-1,6-glucan-binding protein that is a β-1,6-glucanase mutant having no cleavage activity of a β-1,6-glucan and having specific binding activity to a β-1,6-glucan, the third fusion protein comprises a β-1,3-glucan-binding protein, in the first step, when a β-1,6-branched β-1,3-glucan is contained in the test specimen, the active reporter protein comprising the first subunit and the other subunit of the split reporter protein pair is formed as a result of binding of the β-1,6-branched β-1,3-glucan to the first fusion protein and the second fusion protein of reagent (A), when a β-1,3-glucan is contained in the test specimen, the active reporter protein comprising the first subunit and the other subunit of the split reporter protein pair is formed as a result of binding of the β-1,3-glucan to the first fusion protein and the third fusion protein of reagent (B); and a second step of detecting and quantifying a product obtained by performing the first, step wherein the product comprises a detectable signal produced by the formation of the active reporter protein.

2. The method of claim 1, wherein the first fusion protein is a fusion protein in which the first subunit of the split reporter protein is fused to the N-terminal side or C-terminal side of the β-1,3-glucan-binding protein, the second fusion protein is a fusion protein in which the other subunit of the split reporter protein is fused to the N-terminal side or C-terminal side of the β-1,6-glucan-binding protein, and the third fusion protein is a fusion protein in which the other subunit of the split reporter protein is fused to the N-terminal side or C-terminal side of the β-1,3-glucan-binding protein.

3. The method of claim 1, wherein the test specimen is insoluble.

4. The method according to claim 2, wherein the test specimen is insoluble.

5. A kit for detecting and quantifying a β-1,6-branched β-1,3-glucan or a β-1,3-glucan, the kit comprising a reagent (A) and a reagent (B), wherein the reagent (A) comprises a first fusion protein, a second fusion protein and a split reporter protein that has a first subunit and other subunit, wherein the first and other subunits form a pair, and the first fusion protein is linked to the first subunit of the split reporter protein and the second fusion protein is linked to the other subunit of the split reporter protein, wherein the reagent (B) comprises the first fusion protein, a third fusion protein and the split reporter protein that has a first subunit and other subunit, the first fusion protein is linked to the first subunit of the split reporter protein, the third fusion protein is linked to the other subunit of the split reporter protein, wherein the first and other subunits of the split reporter protein form an active reporter protein by making a pair of the first and other subunits of the split reporter protein, the first fusion protein comprises a β-1,3-glucan-binding protein, the second fusion protein comprises a β-1,6-glucan-binding protein that is a β-1,6-glucanase mutant having no cleavage activity of a β-1,6-glucan and having specific binding activity to a β-1,6-glucan, the third fusion protein comprises a β-1,3-glucan-binding protein.

* * * * *

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: peptide linker

<400> SEQUENCE: 1

Asp Asp Ala Lys Lys
1 5

<210> SEQ ID NO 2
<211> LENGTH: 5
<212> TYPE: PRT
<213> ORGANISM: Artificial Sequence
<220> FEATURE:
<223> OTHER INFORMATION: peptide linker

<400> SEQUENCE: 2

Glu Ala Ala Ala Lys
1 5

<210> SEQ ID NO 3
<211> LENGTH: 149
<212> TYPE: PRT
<213> ORGANISM: Artificial Sequence
<220> FEATURE:
<223> OTHER INFORMATION: beta-1,3-glucan-binding protein

<400> SEQUENCE: 3

Met Asn His Lys Val His His His His His His Ile Glu Gly Arg His

-continued

```
1               5                   10                  15

Met Glu Leu Gly Thr Tyr Glu Val Pro Asp Ala Lys Leu Glu Ala Ile
            20                  25                  30

Tyr Pro Lys Gly Leu Arg Val Ser Ile Pro Asp Asp Gly Phe Ser Leu
        35                  40                  45

Phe Ala Phe His Gly Lys Leu Asn Glu Glu Met Glu Gly Leu Glu Ala
    50                  55                  60

Gly Thr Trp Ser Arg Asp Ile Thr Lys Ala Lys Asn Gly Arg Trp Thr
65                  70                  75                  80

Phe Arg Asp Arg Asn Ala Glu Leu Lys Ile Gly Asp Lys Ile Tyr Phe
                85                  90                  95

Trp Thr Tyr Val Ile Lys Asp Gly Leu Gly Tyr Arg Gln Asp Asn Gly
            100                 105                 110

Glu Trp Thr Val Thr Gly Tyr Val Asp Glu Asp Gly Asn Pro Val Asp
        115                 120                 125

Thr Asp Gly Pro Thr Thr Thr Pro Thr Gly Ser Glu Phe Lys Leu Val
    130                 135                 140

Asp Leu Gln Ser Arg
145


<210> SEQ ID NO 4
<211> LENGTH: 450
<212> TYPE: DNA
<213> ORGANISM: Artificial Sequence
<220> FEATURE:
<223> OTHER INFORMATION: sequence encoding beta-1,3-glucan-binding
      protein

<400> SEQUENCE: 4

atgaatcaca aagtgcatca tcatcatcat catatcgaag gtaggcatat ggagctcggt     60

acctatgaag tgcctgatgc gaaactcgaa gccatttacc ccaaagggtt acgcgttagc    120

attccggatg atggcttttc gctgtttgcc ttccatggga aactgaacga ggagatggaa    180

ggtctggaag ctggaacttg gagtcgggac atcacgaaag cgaagaacgg tcgttggacc    240

tttcgtgacc gcaatgcaga gctgaaaatt ggcgacaaga tctacttctg gacctacgtc    300

atcaaagatg gcttgggtta tcgccaggat aacggagaat ggaccgtaac gggctatgtg    360

gacgaagatg gcaatccggt tgataccgat ggtccgacta cgacaccaac cggatccgaa    420

ttcaagcttg tcgacctgca gtctagatag                                     450


<210> SEQ ID NO 5
<211> LENGTH: 9
<212> TYPE: PRT
<213> ORGANISM: Artificial Sequence
<220> FEATURE:
<223> OTHER INFORMATION: linker peptide

<400> SEQUENCE: 5

Gly Gly Ser Gly Gly Gly Ser Gly Gly
1               5
```